United States Patent [19]

Metcalfe et al.

[11] Patent Number: 4,848,162
[45] Date of Patent: Jul. 18, 1989

[54] ELASTODYNAMIC TESTING OF ELONGATE COMPRESSIBLE MATERIAL

[75] Inventors: Raymond Metcalfe, Chalk River; Ronald G. Wensel, Deep River, both of Canada

[73] Assignee: Atomic Energy of Canada Limited, Ottawa, Canada

[21] Appl. No.: 211,926

[22] Filed: Jun. 27, 1988

Related U.S. Application Data

[63] Continuation-in-part of Ser. No. 42,663, Apr. 27, 1987, abandoned.

[30] Foreign Application Priority Data

Dec. 22, 1986 [CA] Canada .................................. 526052

[51] Int. Cl.[4] .............................................. G01N 3/08
[52] U.S. Cl. .................................................... 73/824
[58] Field of Search ................. 73/818, 821, 822, 823, 73/824, 790, 866

[56] References Cited

U.S. PATENT DOCUMENTS

| | | | |
|---|---|---|---|
| 2,342,374 | 2/1944 | Shayne et al. | 73/824 |
| 2,482,147 | 9/1949 | Bashore | 73/823 |
| 3,791,204 | 2/1974 | List et al. | 73/824 |
| 3,796,094 | 3/1974 | Cook et al. | 73/824 |
| 3,803,908 | 4/1974 | Endo et al. | 73/824 |
| 4,077,254 | 3/1978 | Merler et al. | 73/824 |

Primary Examiner—Stewart J. Levy
Assistant Examiner—Robert R. Raevis
Attorney, Agent, or Firm—R. G. Bitner

[57] ABSTRACT

This invention provides non-destructive testing of elongate compressible materials, and particularly to determine the elastodynamic properties of a material, and/or to detect defects such as non-uniformities in resilience or hardness, subsurface as well as surface defects such as inclusions, voids, tears, and the like. The material to be tested is passed between two rollers of substantially contant roller spacing. Measurement of the load provides an indication of elastodynamic properties of the material. Variations in the measured load can be utilized to detect defects in the material. The invention has been found particularly suitable for the testing of material for seals, such as O-rings.

7 Claims, 2 Drawing Sheets

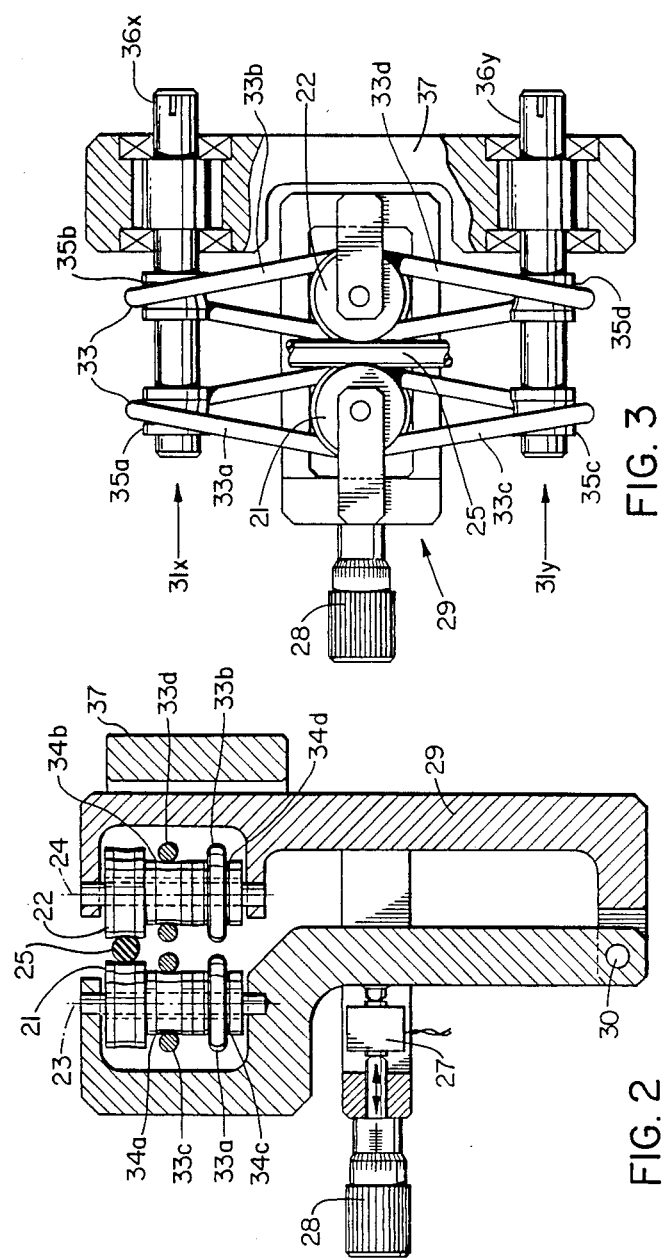

ELASTODYNAMIC TESTING OF ELONGATE COMPRESSIBLE MATERIAL

This is a continuation-in-part of application Ser. No. 042,663, filed Apr. 27, 1987 now abandoned.

FIELD OF THE INVENTION

This invention relates to the determination of elastodynamic properties in elongate compressible materials, and particularly for detecting substandard qualities, defects or non-uniformities in material used for seals.

BACKGROUND OF THE INVENTION

The quality of elastomeric products, such as seals, may be affected by various factors such as variations in dimensions, non-uniformities or overall substandard properties of resilience or hardness, subsurface as well as surface defects such as inclusions, voids, tears, and the like.

Surface defects, or variations in the dimensions of such articles can be detected visually or by using automated profilometry, optical, or other techniques. However, such techniques do not detect subsurface defects, non-uniformities or overall substandard properties of the material.

Other techniques, such as ultrasonics and radiography, that are used for detecting subsurface defects in certain other materials, have serious disadvantages when applied to polymeric materials due to the high damping and small density variations that a defect represents in such a material.

Prior to the making of the present invention, a technique somewhat analogous to a method known for the testing of tires was tried. This involved placing an O-ring to be tested on a rim of matched size and detecting variations in load when rolled against a roller under pressure. This approach, however, was found not to be satisfactory. The use of a rim produced spurious results that were seen to be caused be effects related to the combined structure of the O-ring and rim, for example, due to slipping and folding along the O-ring to rim interface.

Also, this approach necessitated stretching of the O-ring onto the rim which could not be done completely uniformly and which effectively masked any material defects close to the rim while accentuating any rim defects. It was also impractical for testing O-rings of many sizes, with a new rim being necessary for each new size.

SUMMARY OF THE INVENTION

It has been found that elastodynamic properties of elongate materials or an indication of uniformity can be determined by passing the material between two driven compression rollers at substantially constant roller spacing, and measuring compression load.

The term "elastodynamic properties" as used herein refers to properties such as resilience, elasticity, plasticity and creep, and the time and rate of deformation dependence of the elastic and plastic characteristics.

BRIEF DESCRIPTION OF THE DRAWINGS

FIG. 2 is a sectioned view of another embodiment of the invention.

FIG. 3 is a top view of the device shown in FIG. 2.

DESCRIPTION OF PREFERRED EMBODIMENTS

Figure 1:
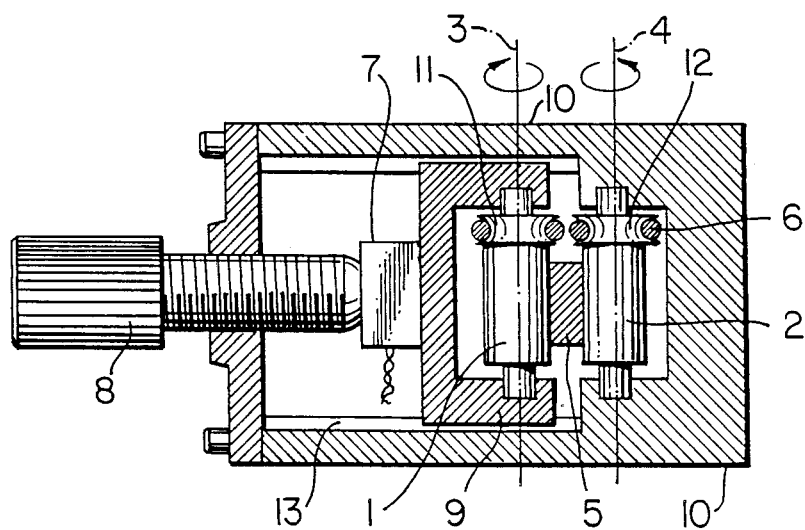
FIG. 1 is a partially sectioned view of one embodiment of the invention.

With reference to FIG. 1, the apparatus comprises a pair of opposed compression rollers 1 and 2 rotatably mounted on axes 3 and 4. The rollers are mounted on slidably interconnected support members 9 and 10. The rollers are disposed to compress a compressible test material 5 as it is passed between the rollers 1 and 2. The compression rollers 1 and 2 are driven by drive means that comprise a drive pulley 11 and 12, connected with compression roller 1 and 2, respectively. Each drive pulley is driven by resilient means in the form of a belt 6. Sensing means 7, operatively connected between the compression rollers 1 and 2, indicate the compression load transmitted to the rollers as the material 5 is passed between the rollers 1 and 2.

The sensing device 7 may, for example, be a commercial load cell. Adjustment means 8 provides for adjustment of the spacing between rollers 1 and 2, to accommodate materials of different dimensions. The members 9, on which roller 1 is mounted, is slidably mounted by means of a linear bearing and includes suitable guide means 13 that prevents rotation of member 9 relative to the member 10.

Preferably, as shown, the belts 6 will be oriented normal to a plane containing a central longitudinal axis of both compression rollers 1 and 2, to reduce sensitivity by the sensing means 7 to forces in the drive means.

In operation, the desired spacing of the compression rollers is adjusted for the test material 5, with the use of the adjustment means 8. As the material 5 passes between the rollers 1 and 2, driven by belts 6, the output of the sensing device 7 will provide an indication of the elastodynamic properties of the material, with variations in the output providing an indication of defects or non-uniformities in the material. The output may be used to determine elastodynamic properties such as resilience, elasticity, plasticity or creep, under specified operating conditions, or properties may be indicated by comparison with the output under similar conditions from a reference specimen. Alternatively, or additionally, testing may be for the purpose of detecting non-uniformities, for example, defects, within a particular sample, by detecting or measuring variations in output.

FIGS. 2 and 3 show another embodiment of the invention.

The compression rollers 21 and 22 are driven by means that includes a first drive pulley 34 coaxially connected with each compression roller, a second pulley 35 spaced from the first drive pulley 34 and mounted on a drive shaft 36 that is connected with a suitable power source (not shown) and counter-rotated at substantially the same speed.

FIGS. 2 and 3 shows a pair of drive units $31x$ and $31y$ and includes a pair of each of the first drive pulleys 34, second drive pulleys 35 and drive belts 33 associated with each of the compression rollers. Specifically, drive unit $31x$ comprises first drive pulleys $34a$ and $34b$, second drive pulleys $35a$ and $35b$, belts $33a$ and $33b$, and drive shaft $36x$. Similarly, drive unit $31y$ comprised first drive pulleys $34c$ and $34d$, second drive pulleys $35c$ and $35d$, belts $33c$ and $33d$, and drive shaft $36y$. The drive units $31x$ and $31y$ each includes a drive shaft $36x$ and $36y$ respectively. These two shafts, $36x$ and $36y$, are interconnected by support member 37 and each have coaxially connected thereto two of the second drive pulleys $35a$, $35b$ and $35c$, $35d$ respectively, arranged such that the compression roller assembly 29 can be suspended by the four drive belts 33, providing isolation from vibration from the drive means. The support means 37 for the drive shafts 36 is isolated from the support means 29 for the compression rollers 21 and 22 to avoid transfer of vibration.

It will be noted that the first drive pulleys 34 and the second drive pulleys 35 are oriented relative to the compression rollers 21 and 22 such that an axis passing centrally through said first and second pulleys intersecting their axis of rotation is substantially normal to a plane containing a central longitudinal axis of both compression rollers, to reduce sensitivity by the sensing means to forces in the drive means.

The preferred sensing means is in the form of a load cell 27. It will be understood that the operation of most load sensing devices inherently results in a certain amount of displacement change so that an absolutely constant roller spacing cannot be readily obtained. However, this displacement can be made so small as to be negligible.

Either of the embodiments disclosed can be used with various types of test procedures or conditions that can be used to reveal different properties in the test material. The compressive deformation and rate of passing between the roller, including appropriate intermittent or discontinious operating conditions, enables the time and rate of deformation dependence of the elastic and plastic behaviour to be determined or compared with a reference specimen.

The magnitude of compression load applied will depend on the particular material and the information desired. For example, it was found that performing a test with relatively low compression provided higher sensitivity to defects near the surface of the article, and higher compression increased the sensitivity to deeper defects.

Multiple tests can be used to reveal a variety of properties. As suggested above, tests conducted under both low and high degrees of compression can be used to reveal whether a defect is near the surface. Test runs at different speeds will indicate whether the material is sensitive to the rate of deformation. A measure of creep or compression set can be provided by discontinuous testing. This involves stopping the article for a period of time in one position under compression, and detecting the non-uniformity retained in a subsequent pass. All tests can be done at various temperatures, or other environmental conditions, to assess the effects of such conditions on the material.

The present invention may be used for testing various compressible materials, such as seals, belting, flooring, and the like.

We claim:

1. A method of indicating elastodynamic properties of elongate compressible material comprising:

introducing the material between a pair of opposed compression rollers;

driving the rollers by means of resilient drive means oriented relative to the compression rollers to reduce transfer of drive force to sensing means;

compressing the material as it passes between the rollers at substantially constant spacing; and sensing compression load transmitted to the rollers via the sensing means as the material passes between the rollers.

2. The method of claim 1 further comprises detecting variations in compression load for indicating non-uniformities in the material.

3. An apparatus for indicating elastodynamic properties of elongate compressible material comprising:

a pair of opposed compression rollers;

support means for supporting the rollers in a spaced relation at substantially constant spacing for applying compression to material passing between the rollers;

sensing means, operatively associated with the compression rollers, for sensing compression load as the material passes between the rollers; and drive means for driving the compression rollers, said drive means comprising a first drive pulley coaxially connected with each of said compression rollers, a second drive pulley operatively associated with, and spaced from each of said first drive pulleys, and drive belt means for interconnecting each of said first and second drive pulley, said first and second drive pulleys being oriented relative to the compression rollers such that a central axis passing centrally through said first and second pulleys and intersecting their axis of rotation is substantially normal to a plane containing a central longitudinal axis of both of the pair of spaced compression rollers, to reduce sensitivity by the sensing means to forces in the drive means.

4. The apparatus of claim 3, further comprising means for adjusting the spacing of the compression rollers.

5. The apparatus of claim 3, further comprising support means for the second drive pulley substantially isolated from the support means for the compression rollers to avoid transfer of vibration.

6. The apparatus of claim 3 comprising a pair of each of said first and second drive pulleys and wherein the drive belt means comprises a pair of drive belts associated with each of said compression rollers, and including a pair of drive shafts each coaxially connected with two of the second drive pulleys, and wherein the drive shafts are spaced from one another on opposite sides of the compression rollers whereby the compression rollers are effectively suspended by the drive belts.

7. The apparatus of claim 6 wherein the pair of second drive pulleys are coaxially mounted on a common drive shaft.

* * * * *